United States Patent
Lagodzki et al.

(10) Patent No.: US 9,788,839 B2
(45) Date of Patent: Oct. 17, 2017

(54) STABLE SCREW-TYPE DETACHMENT MECHANISM

(71) Applicant: Cook Medical Technologies LLC, Bloomington, IN (US)

(72) Inventors: Karol Lagodzki, Bloomington, IN (US); Tyler Turk, Greenwood, IN (US); Trevor Plassman, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 231 days.

(21) Appl. No.: 14/621,565

(22) Filed: Feb. 13, 2015

(65) Prior Publication Data

US 2015/0230802 A1   Aug. 20, 2015

Related U.S. Application Data

(60) Provisional application No. 61/939,880, filed on Feb. 14, 2014.

(51) Int. Cl.
*A61B 17/12* (2006.01)

(52) U.S. Cl.
CPC .... *A61B 17/12109* (2013.01); *A61B 17/1214* (2013.01); *A61B 17/12113* (2013.01); *A61B 2017/12095* (2013.01)

(58) Field of Classification Search
CPC .......... A61B 17/12109; A61B 17/1213; A61B 17/1214; A61B 2017/12095
See application file for complete search history.

(56) References Cited

U.S. PATENT DOCUMENTS

| | | | |
|---|---|---|---|
| 5,234,437 A | 8/1993 | Sepetka | |
| 5,312,415 A | 5/1994 | Palermo | |
| 5,421,348 A * | 6/1995 | Larnard | A61M 25/0905 600/434 |
| 5,626,613 A * | 5/1997 | Schmieding | A61B 17/0401 24/711.3 |
| 5,725,534 A | 3/1998 | Rasmussen | |

(Continued)

FOREIGN PATENT DOCUMENTS

| | | |
|---|---|---|
| EP | 1120088 A1 | 8/2001 |
| WO | WO 94/06502 | 3/1994 |
| WO | WO 2009/036219 A1 | 3/2009 |

*Primary Examiner* — Julie A Szpira
(74) *Attorney, Agent, or Firm* — Brinks Gilson & Lione

(57) ABSTRACT

An occluding device apparatus includes an embolization coil with a distal end and a proximal end with an opening and an attacher that is threaded through the opening at the proximal end of the embolization coil. The apparatus further comprises a delivery kit for delivery of the embolization coil in a body cavity. The kit comprises a guide catheter for percutaneous introduction of the embolization coil and an inner catheter slidably disposed within the guide catheter during insertion. The inner catheter comprises a proximal end and a distal end. The inner catheter further includes a hub disposed adjacent the proximal end. The kit further comprises a guide wire slidably disposed within the inner catheter. The guide wire provides a path during insertion thereof within a body cavity. The kit further comprises a pushwire to advance the embolization coil through the inner catheter.

16 Claims, 5 Drawing Sheets

(56) References Cited

U.S. PATENT DOCUMENTS

| | | | |
|---|---|---|---|
| 5,725,546 A * | 3/1998 | Samson | A61B 17/12022 606/191 |
| 7,344,558 B2 * | 3/2008 | Lorenzo | A61B 17/12022 623/1.11 |
| 7,722,636 B2 * | 5/2010 | Farnan | A61B 17/12022 606/200 |
| 8,062,325 B2 * | 11/2011 | Mitelberg | A61F 2/95 606/200 |
| 8,308,753 B2 | 11/2012 | Gesswein et al. | |
| 2002/0004676 A1 | 1/2002 | Wallace et al. | |
| 2006/0111771 A1 * | 5/2006 | Ton | A61F 2/88 623/1.15 |
| 2006/0116709 A1 | 6/2006 | Sepetka et al. | |
| 2007/0083219 A1 | 4/2007 | Buiser et al. | |
| 2007/0123927 A1 * | 5/2007 | Farnan | A61B 17/12022 606/200 |
| 2007/0123928 A1 | 5/2007 | Farnan | |
| 2010/0121350 A1 | 5/2010 | Mirigian | |
| 2014/0257361 A1 * | 9/2014 | Prom | A61B 17/12022 606/198 |
| 2014/0257373 A1 * | 9/2014 | Prom | A61B 17/12022 606/213 |
| 2015/0025310 A1 * | 1/2015 | Everingham | A61F 6/18 600/103 |

* cited by examiner

STABLE SCREW-TYPE DETACHMENT MECHANISM

CROSS REFERENCE TO RELATED APPLICATIONS

This application claims the benefit of U.S. Provisional Patent Application No. 61/939,880 filed Feb. 14, 2014, the content of which is hereby incorporated by reference in its entirety.

BACKGROUND

The embodiments of the present invention relate to medical devices. More particularly, the embodiments relate to assemblies for deploying medical devices including occluding devices into a body cavity.

Medical devices such as embolization coils and plugs have been used as a primary occluding device for treatment of various arteriovenous malformations (AVM) and varicoceles, as well as for many other arteriovenous abnormalities in the body. Occluding devices are also used to repair abnormal shunts between arteries and veins, prevent or reduce blood flow to tumors, stop hemorrhaging as a result of trauma, and stabilize aneurysms to prevent rupture. Embolization coils, for example pushable fibered coils, may be made in a variety of sizes with varying diameters and may be made of several different materials including stainless steel and platinum. Occlusion devices may vary for differing purposes, e.g., to hold the device in place within a cavity or vessel and to pack the device within the vessel for enhanced occlusion.

Although current devices are adequate, in some cases delivery of such coils or plugs may be improved for more effective occlusion of fluid flow through a lumen of a body vessel. Many medical procedures for occluding blood flow through an artery or vein require a number of coils, since a single coil or two may not be sufficient to effectively occlude blood flow through a lumen of an artery or vein. In some cases, delivery of such a coil or a plug can involve pushing a coil through the lumen of a delivery catheter using a pusher element. In other cases, the device, such as the coil or plug, can be receive a threaded end of a delivery device, and the practitioner deploying the device can use rotational force to separate the device from the delivery mechanism.

In certain cases, delivery can be complicated because without some sort of external surface pushing back against the rotation, the device may simply rotate with the delivery member rather than becoming disengaged from it. In many cases, the external friction is derived from contact with the wall of the vessel in which the device is being deployed. This can be disadvantageous when the body cavity to which the device is being deployed is particularly delicate, such as in an aneurysm.

BRIEF SUMMARY OF THE INVENTION

There is a need for an improved means of delivery of medical devices such as coils and plugs into body cavities. The medical device described herein provides an assembly for and a method of delivering a device into the lumen of a body vessel.

In one aspect, the present invention is a medical device delivery assembly comprising a medical device to be deployed having a first proximal end and a first distal end. The first proximal end has a first interior lumen and a first outer surface with at least one prong being attached to the first outer surface of the first proximal end. The assembly has a delivery portion having a second proximal end and a second distal end. The delivery portion having a second interior lumen and a second outer surface, the second interior lumen being sized so as to fit the first proximal end of the medical device to be deployed therein. The second distal end of the delivery portion has at least one notch which receives the at least one prong of the medical device to be deployed. The assembly further comprises a mandrel having a third proximal end and a third distal end and slidably disposed within the interior lumen of the second interior lumen of the delivery portion, the third distal end of the mandrel fitting within the first interior lumen of the first proximal end of the medical device to be deployed. In another form, the occluding device includes an embolization coil with a distal end and a proximal end and a suture or an attacher that is tied as a slip-knot around the proximal end of the embolization coil.

In another aspect, the present invention is a method of deploying a medical device in a body cavity. The method provides a medical device having a first proximal end and a first distal end, the first proximal end having a first interior lumen and a first outer surface, at least one prong being attached to the first outer surface of the first proximal end. The method provides a delivery portion having a second proximal end and a second distal end, the delivery portion having a second interior lumen and a second outer surface. The second interior lumen is sized so as to fit the first proximal end of the medical device to be deployed therein. The second distal end of the delivery portion has at least one notch which can receive the at least one prong of the medical device to be deployed. The method then comprises threading a mandrel having a third proximal end and a third distal end, the third distal end being threaded, into the first interior lumen of the first proximal end of the medical device to be deployed. The mandrel is inserted into the second interior lumen of the delivery portion. The medical device and the delivery portion are then introduced into a patient percutaneously, and the device is maneuvered to the location where the device is to be delivered. The mandrel is then rotated until the third distal end of the mandrel is no longer within the first interior lumen of the medical device, and the medical device is released into the body cavity.

In a third aspect, the present invention is a kit for deploying a medical device to a body cavity. In this embodiment, the kit comprises a medical device to be deployed having a first proximal end and a first distal end, the first proximal end having a first interior lumen and a first outer surface and at least one prong being attached to the first outer surface of the first proximal end. The kit provides a sheath for positioning the medical device in the body cavity comprising a delivery portion having a second proximal end and a second distal end, the delivery portion having a second interior lumen and a second outer surface. The second interior lumen is sized so as to fit the first proximal end of the medical device to be deployed therein. The second distal end of the delivery portion has at least one notch which can receive the at least one prong of the medical device to be deployed. The kit also provides a mandrel having a third proximal end and a third distal end and slidably disposed within the interior lumen of the second interior lumen of the delivery portion, the third distal end of the mandrel which can fit within the first interior lumen of the first proximal end of the medical device to be deployed.

Further features and advantages will become apparent from the following description and from the claims.

DETAILED DESCRIPTION OF THE INVENTION

This description is not intended to limit the present invention in any manner, but rather serves to enable those skilled in the art to make and use the invention.

The terms "substantially" or "about" used herein with reference to a quantity or shape includes variations in the recited quantity or shape that are equivalent to the quantity or shape recited, such as an amount or physical conformation that is equivalent to the quantity or shape recited for an intended purpose or function.

A medical device may be deployed to a body cavity and employed for treatment of a number of conditions in which partial or complete occlusion of a body cavity is desired, including but not limited to renal arteriovenous malfunction (AVM), pulmonary AVM, vascular tumors, low-flow fistulas, trauma related hemorrhages, and visceral vasculature defects including varicoceles, aneurysms, and selected telangiectasias. For example, treatment of visceral vasculature defects may include but are not limited to embolotherapy on gastroduogenal hemorrhages, hepatic aneurysms, celiac aneurysms, internal iliac aneurysms, and internal spermatic varicoceles.

Although occluding devices are explicitly named in the proceeding, it is another intended aspect of this invention to provide a delivery assembly that allows for reliable and convenient detachment of any medical device. In this aspect, the medical device which is intended to remain in the lumen of a body cavity or vessel as a permanent or temporary method of treatment.

Figure 1:
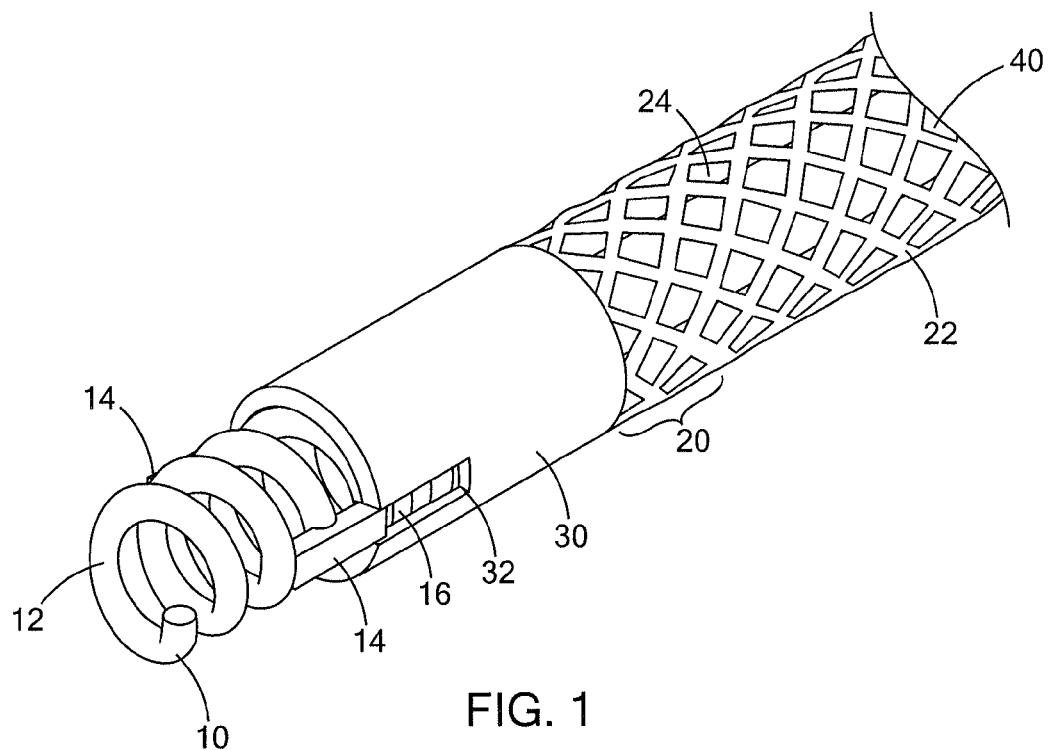
FIG. 1 is a perspective view of a medical device partially engaged with a delivery assembly in accordance with one embodiment of the present.

FIG. 1 shows a medical device 10 and medical device delivery assembly in accordance with one embodiment of the present invention. As shown, the device 10 is positioned extending out of interior lumen 24 of delivery catheter 20.

As illustrated in FIG. 1, device 10 is an occluding coil comprising a first proximal portion 16 and a first distal portion 12. In one aspect, the medical device (in this case, a coil) extends from the first proximal end 16 to the first distal end 12. The device 10 is illustrated in truncated form for clarity and the illustration is not intended to limit the length of the coil in the distal direction, nor does it limit the type of device that can be employed to a coil. Device 10 also includes a pair of rail structures 14 toward its proximal end. The rail structures 14, alternately termed rails 14, are illustrated as rectangular blocks for simplicity but may be of other shapes such as rounded shapes, elliptical shapes, triangular shapes, or any other shapes which may reasonably fitted into a corresponding receiving element.

The rails 14 can be made of any suitable material, including metal or rigid polymer, and can either be prefabricated as a component of the device 10 or can be separately formed and attached after manufacture. There can be a single rail, or a plurality of rails 14. The rails can vary in shape, in length, and in width. The rails 14 can be evenly spaced around the perimeter of the first proximal portion 16 of the medical device 10 or the rails 14 can be biased to one portion of the device. Although the rails 14 of FIG. 1 are illustrated as being the same size and shape as one another, it is not necessary that they are. For instance, one rail 14 of a device 10 can be substantially rectangular while a second rail 14 is substantially circular.

The rails 14 can be fixed at any point axially along the length of the device 10. In cases of devices 10 with a relatively short length, the rails may be extend the entire length of the device. In other devices, the rails 14 may be set at a point substantially closer to the proximal end than to the distal end of the device 10. In this case, the effect will be that the device 10 will be both disengaged from the locking assembly comprising the rails and notches, but a portion of the device 10 will remain within the delivery catheter. Various embodiments reflecting the fact that the rails 14 can be placed at different positions along the axial length of device 10 are depicted in the drawings. However, the rails 14 will be fixed at approximately the same axial position on the device such that when the device is rotably disengaged from the mandrel, the whole device is free to move independent of the delivery assembly.

The delivery catheter 20 of FIG. 1 is further subdivided into two portions: a second proximal portion 26 and a second distal portion 28. In one aspect, the second proximal portion 26 extends to the second distal portion 28. As illustrated, the second proximal portion can comprise a braid 22. If a braided catheter is used, it may be made of materials including but not limited to high tensile stainless steel, such as 304V stainless steel wire, tungsten, gold, titanium, silver, copper, platinum, palladium, iridium, nickel-cobalt alloys, cobalt chrome alloys, molybdenum tungsten alloys, tantalum alloys, and titanium alloys. Some metals, such as tungsten and tungsten alloys, may be preferred to permit improved visualization of the assembly.

Other tubular catheter assemblies which are not braided are acceptable for use in this assembly. The catheter can be made of any suitable material, including a shape memory polymer or another plastic. The catheter has an interior lumen 24 which is wide enough to fit mandrel 40 within.

Second distal portion 28 of the delivery catheter comprises outer tube 30. Outer tube 30 has at its distal end at least one notch 32. The notches 32 are equal in number to the rails 14 of the device 10 which is to be deployed, and their size and shape are such that they are capable of receiving and securely engaging the rails 14. The outer tube 30 has a number of notches 32 to receive the rails 14 in sufficient quantity so that all notches are accommodated. For instance, as illustrated in FIG. 1, the rectangular rails 14 are of a size and shape that they will fit into notches 32.

Outer tube 30 may be attached to the second proximal portion of the delivery catheter in any suitable way. The outer tube 30 may be soldered or welded onto the distal end of the second proximal portion 26, or the distal end of the second proximal portion may be crimped to a size where it can be snugly placed within an interior lumen of outer tube 30. The outer tube 30 can be made of rigid or flexible material, of metal, polymer, or plastic, as long as it is able to receive and securely engage the rails 14.

In an alternative embodiment, the at least one notch 32 can be formed from the distal end of a delivery catheter during or after its manufacture instead of attaching a separate outer tube 30 to the distal end of the delivery catheter.

Figure 2A:
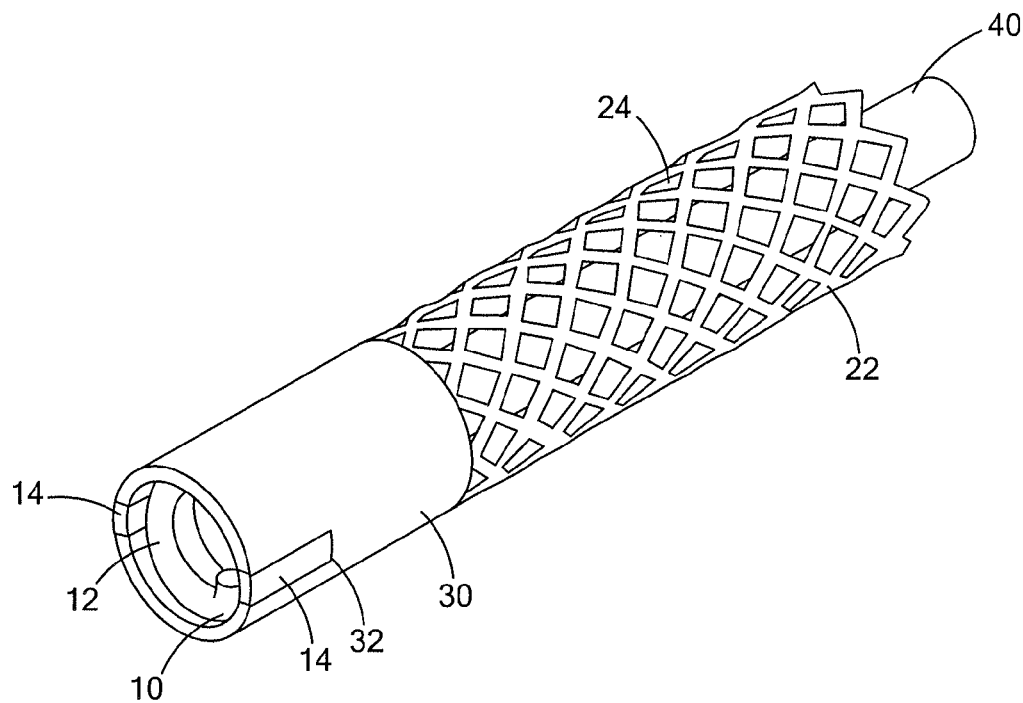
FIG. 2A is a perspective view of the medical device fully engaged with the delivery assembly.

As illustrated in FIG. 2A, first proximal portion 16 of the medical device 10 is sized to fit into the interior lumen of outer tube 30. As in FIG. 1, the portion of the medical device distal to the portion illustrated is not shown for purposes of clarity.

Figure 2B:
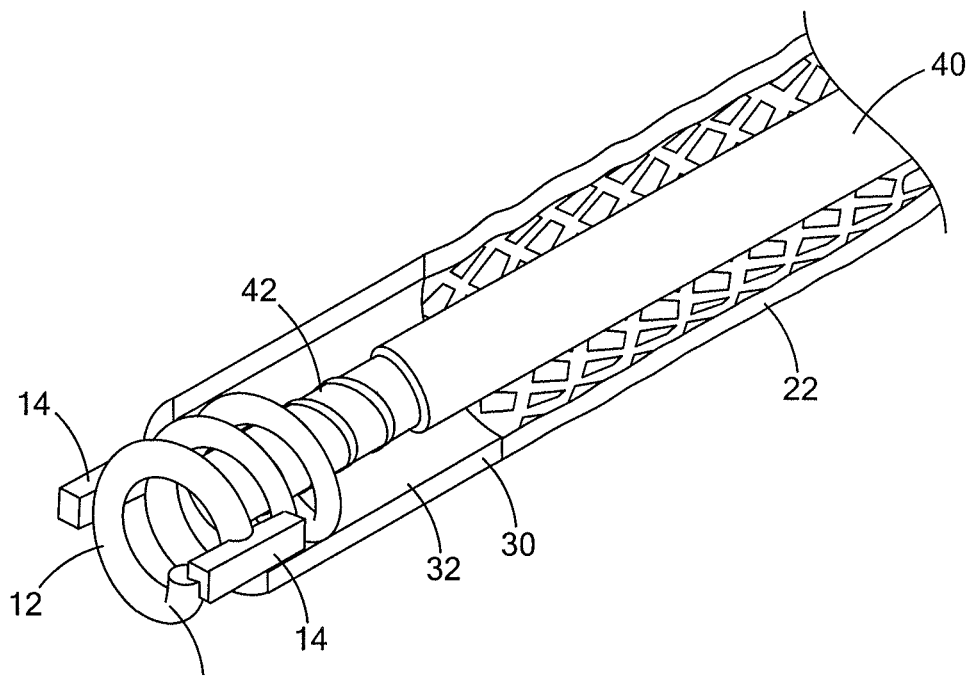
FIG. 2B is a cutaway perspective view of the medical device fully engaged with the delivery assembly.

FIG. 2A and 2B represent an initial delivery configuration for the delivery assembly. The medical device 10 would be engaged with mandrel 40 via threads 42 and packed for delivery with the at least one rails 14 seated in at least one notches 32. A device in this configuration would be longitudinally locked; that is, the engagement of the device 10 with the threads 42 of mandrel 40 would prevent motion along the longitudinal axis of the delivery catheter 20, preventing accidental slippage of the device off of the end of the mandrel 40 and into an undesired position within the body cavity prior to intended deployment. Pushing the mandrel alone, without rotational force, will not dislodge the coil into the lumen of the body cavity or vessel.

In one embodiment, the first proximal portion 16 of the medical device 10 which can be housed within the interior of the outer tube 30 is relatively short in length, for instance no longer than about 3 millimeters. Because the delivery assembly may need to maneuver through relatively tortuous portions of the vasculature or other parts of the anatomy, the relatively stiff outer tube 30 should be kept to a smaller length.

Figure 3:
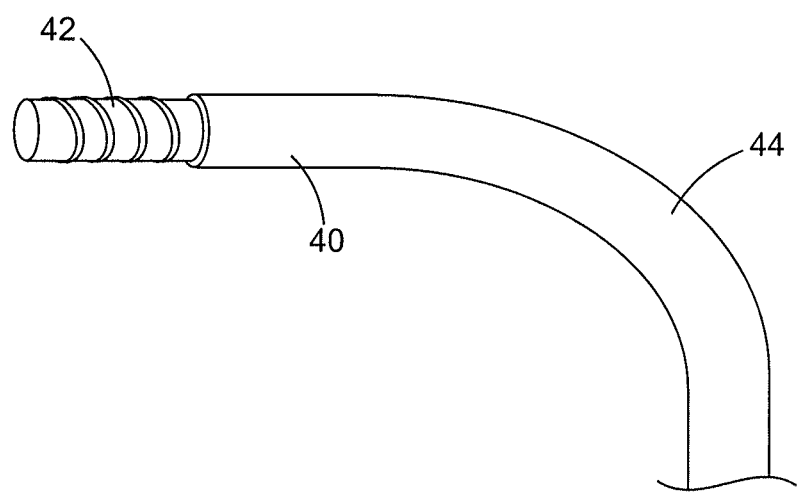
FIG. 3 is a partial side view of a mandrel of the delivery assembly.

As shown in FIG. 3, the mandrel 40 is another component of the medical device delivery system. The mandrel comprises a third distal end 48 which has threads 42 and extends to a third proximal end 46, which the physician uses to rotate and thereby move the device 10 from its engaged to disengaged state. The mandrel is made of a flexible material, such as a shape memory metal or a flexible polymer, as shown by bend 44. The mandrel is made of a flexible material in order to facilitate negotiation of tortuous portions of the anatomy.

Figure 4:
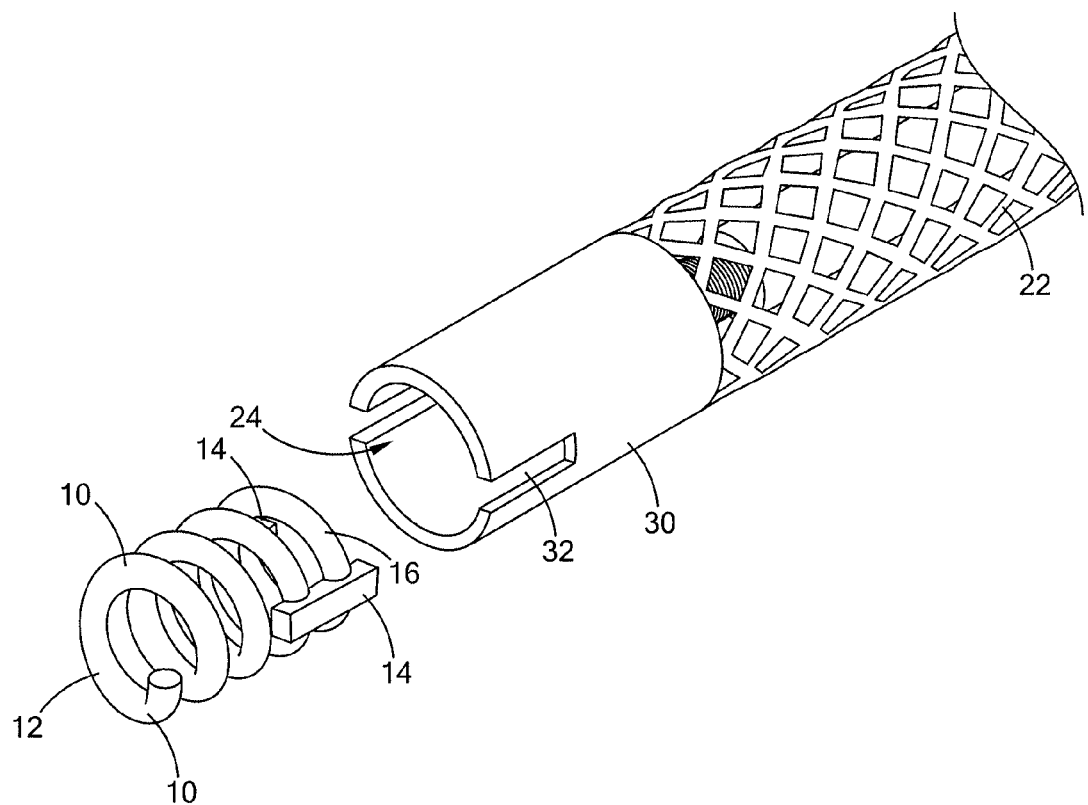
FIG. 4 is a perspective view of the medical device disengaged from the delivery assembly.

FIG. 4 illustrates another embodiment of the invention of this disclosure. In this case, the interventionalist has rotated the mandrel 40 and the device 10 has been disengaged from threads 42 of the mandrel 40. Note that rails 14 of the device continue to be associated with the device. Although the embodiment illustrated in FIG.1, 2A, 2B, and 4 shows rails 14 as a component of the device to be delivered, it is also envisioned that an inverted configuration wherein the rails 14 comprise a portion of delivery catheter 20 and the notches 32 are instead on the proximal end of device 10.

As mentioned, the process of preparation of a device for deployment begins with seating the prongs or rails 14 within the notches 32. Then the third distal end of a mandrel, which is threaded, is threaded into the interior of the medical device 10 with the mandrel also passing into the second interior lumen of the delivery portion.

In the interventional suite, the medical device and the delivery portion are introduced into a patient percutaneously and the device is maneuvered to the location (that is, the body cavity or the body vessel where the device is to be delivered) buy using a pushing force. When the desired location has been reached the mandrel is rotated by the interventionalist at its third proximal end until the third distal end of the mandrel is no longer within the first interior lumen of the medical device, thereby releasing the medical device into the body cavity.

One advantage of such a method is that the delivery assembly does not need to gain purchase on the vessel wall during delivery and deployment in order to create a mechanical force that allows for rotation of the mandrel without concomitant rotation of the device. Such force is instead generated from contacting the rails 14 with the outer tube 30 within notches 32, keeping the device itself stationary as the mandrel alone rotates and becomes disengaged from the device. When the mandrel is freed from the first proximal end 16 of the device 10, the device 10 is no longer kept in place and can thus move in longitudinally in the distal direction in order to be deployed to the body cavity or vessel. When the threads 42 of the mandrel 40 are disengaged from the device 10, the device 10 is effectively considered to be in the deployed state.

Figure 5A:
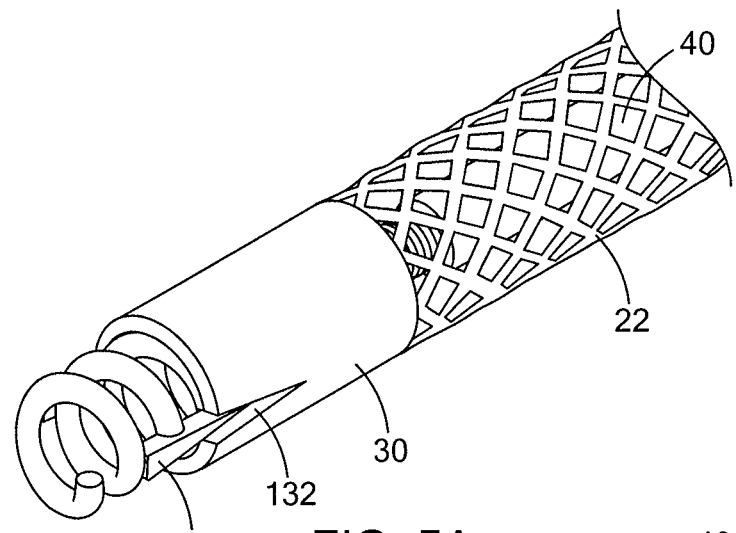
FIG. 5A-C are perspective views of medical devices and delivery assemblies.
Figure 5B:
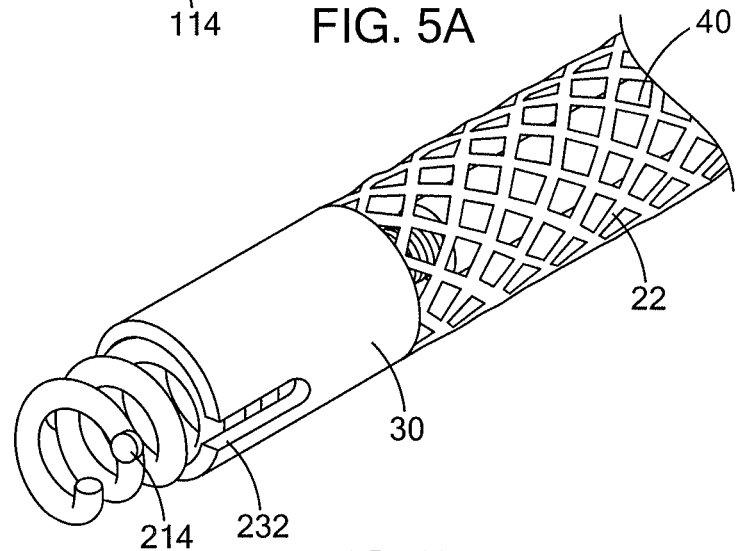
Figure 5C:
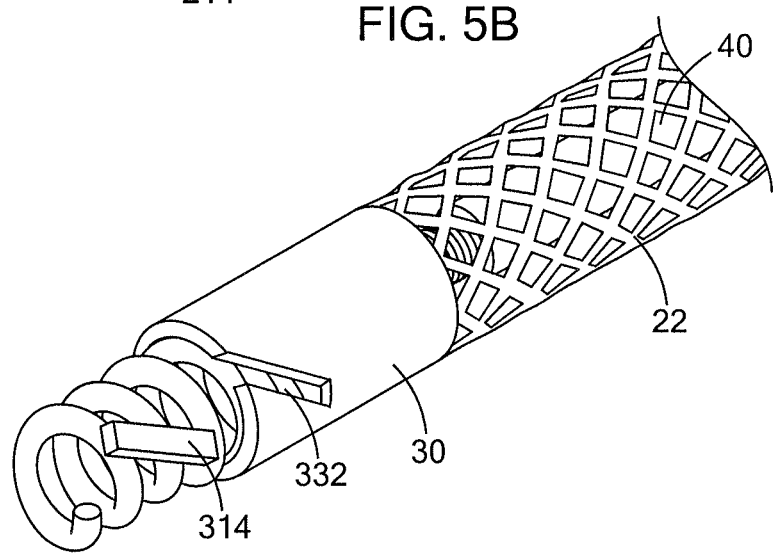

FIG. 5A-5C illustrate alternative embodiments of the medical device delivery assembly. In each case, alternative configurations of rails 114/214/314 are shown with their respective notches 132/232/332. In FIG. 5A, the rails 114 and notches 132 are substantially triangular. In FIG. 5B, the rails 214 are relatively small circular-shaped points which are able to slide into notches 232. Note that although the lengthwise size of the rails is shortened, the notches themselves are still of approximately the same lengths in other embodiments. Finally, in FIG. 5C a single-rail, single-notch device is shown. In this embodiment, notch 332 is not parallel to the longitudinal axis, and rail 314 is likewise at an angle. Still, when rotational force is applied to the mandrel, the rail will be gradually expelled from the notch 332 and will altogether disengage.

The components of the invention of this disclosure, including the rails, the notches, and the outer tube of the delivery catheter, can be made as portions of entirely new devices or can exist as modifications to well-known devices. One particular device which would benefit from improvements as listed above is the microcoil. These coils are small and must occasionally be deployed into difficult-to-access portions of the anatomy. As such, the extra precision gained from using a screw-type delivery assembly would be a benefit in delivering these devices.

As mentioned, the device 10 may preferably be an embolic coil. Such a coil may be made of primary and secondary coils which are fabricated from shape memory materials or alloys, such as superelastic nickel-titanium alloys. In one embodiment, the diameter of the coil is smaller toward the proximal end 16 in order to keep the width consistent as this is where the rails 14 will be attached. Alternatively, the coil may substantially comprise simply a primary coil. An example of a suitable superelastic nickel-titanium alloy is Nitinol, which can "remember" and recover a previous shape.

Nitinol undergoes a reversible phase transformation between a martensitic phase and an austenitic phase that allows it to "remember" and return to a previous shape or configuration. For example, compressive strain imparted to the coils 18, 28 in the martensitic phase to achieve a low-profile delivery configuration may be substantially recovered during a reverse phase transformation to austenite, such that the coils 18, expand to a "remembered" (e.g., deployed) configuration at a treatment site in a vessel. Typically, recoverable strains of about 8-10% may be obtained from superelastic nickel-titanium alloys. The forward and reverse phase transformations may be driven by a change in stress (superelastic effect) and/or temperature (shape memory effect).

Slightly nickel-rich Nitinol alloys including, for example, about 51% Ni and about 49% Ti are known to be useful for medical devices which are superelastic at body temperature. In particular, alloys including 50.6-50.8% Ni and 49.2-49.4% Ti are considered to be medical grade Nitinol alloys and are suitable for the present coils 18, 28. The nickel-titanium alloy may include one or more additional alloying elements.

Figure 6A:
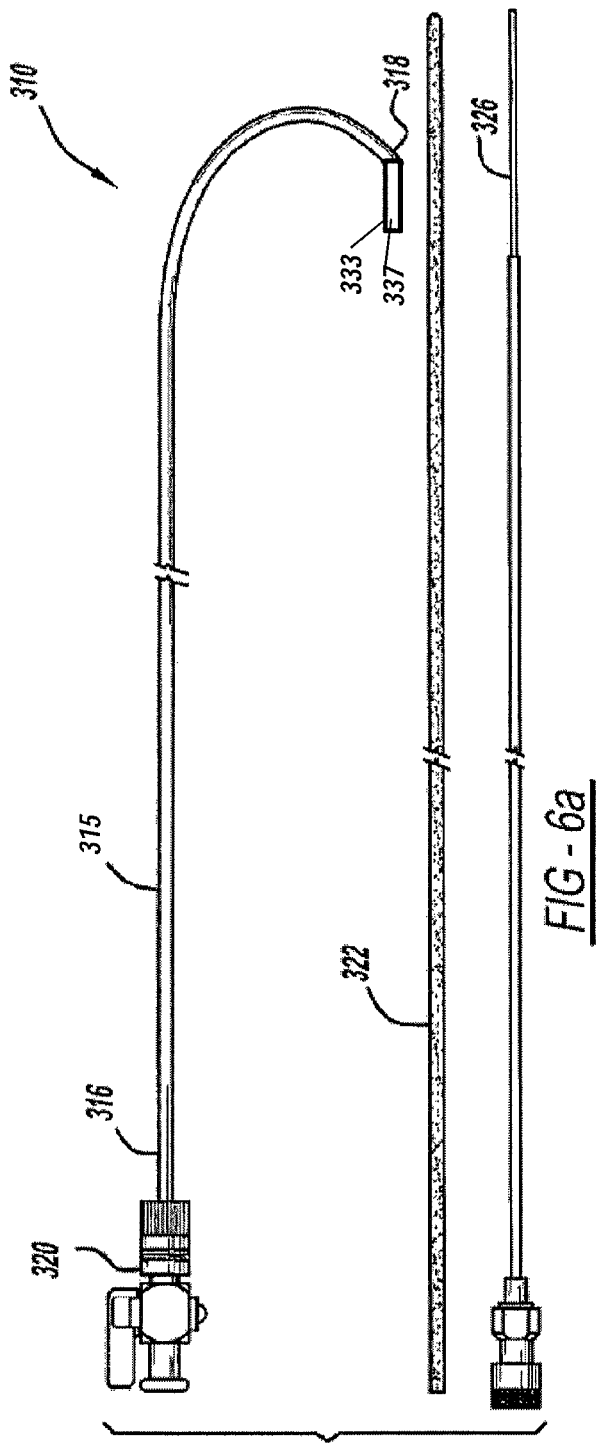
FIG. 6A is an exploded view of an embolization kit.
Figure 6B:
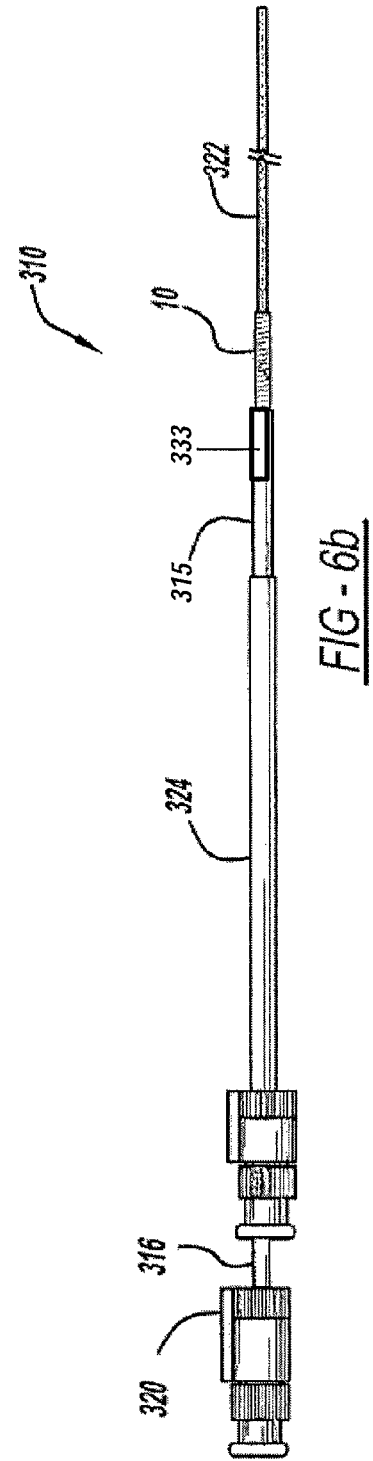
FIG. 6B is a side view of the embolization kit of FIG. 6A.

Turning now to FIGS. 6A and 6B, there is illustrated the embolization kit 310 which implements the occluding device 10. As shown, the kit 310 includes an inner catheter 314 preferably made from a soft, flexible material such as silicone or any other suitable material. Generally, the inner catheter 315 has a proximal end 316, a distal end 318, and an outer tube as an adapter or hub 320 to receive apparatus to be advanced therethrough. The kit 310 further includes a guide wire 322 which provides a path during insertion of the catheter 324 within a body cavity. The size of the wire guide is based on the inside diameter of the guide catheter 324.

In one embodiment, the kit 310 further includes a polytetrafluoroethylene (PTFE) guide catheter or sheath 324 for percutaneously introducing the inner catheter 315 in a body vessel. Of course, any other suitable material may be used. The guide catheter 324 may have a size of about 4-French to 8-French and allows the inner catheter 315 to be inserted therethrough to a desired location in the body cavity. The guide catheter 324 receives the inner catheter 315 and provides stability of the inner catheter 315 at a desired location of the body cavity. For example, the guide catheter 324 may stay stationary within a common visceral artery, e.g., a common hepatic artery, and add stability to the inner catheter 315 as the inner catheter is advanced through the guide catheter to a point of occlusion in a connecting artery, e.g., the left or right hepatic artery.

The medical device 10 has been loaded at distal end 318 of the inner catheter 315. The prongs or rails of the device 10 are interlocked within the notches 337 of the outer tube 333 which is attached to distal end 318 of the inner catheter 315. In this embodiment, a mandrel is used to mechanically advance or push the occluding device 10 through the inner catheter 314 before application of rotational force and deployment of the device. The size of the push wire used depends on the diameters of the inner catheter 315.

It is to be understood that the embolization kit 310 described above is merely one example of a kit that may be used to deploy the medical device in a body cavity or vessel. Other kits, assemblies, and systems may be used to deploy any embodiment of the occluding device without falling beyond the scope or spirit of the present.

The aforementioned as well as other embodiments are within the following claims.

What is claimed is:

1. A medical device delivery assembly comprising:
   a medical device to be deployed, the medical device extending from a medical device proximal end to a medical device distal end, the medical device proximal end comprising a medical device lumen and a medical device outer surface, at least one prong being attached to the medical device outer surface of the medical device proximal end;
   a delivery portion extending from a delivery portion proximal end to a delivery portion distal end, the delivery portion comprising a delivery portion lumen and a delivery portion outer surface, the delivery portion lumen being sized so as to fit the medical device proximal end therein, the delivery portion distal end of the delivery portion comprising at least one notch for receiving the at least one prong of the medical device to be deployed such that when the at least one prong is engaged with the at least one notch, the medical device and the delivery portion rotate together bidirectionally; and
   a mandrel extending from a mandrel proximal end to a mandrel distal end, the mandrel being slidably disposed within the delivery portion lumen of the delivery portion, the mandrel distal end of the mandrel fitting within the medical device lumen of the medical device proximal end of the medical device to be deployed.

2. The medical device of claim 1 wherein the medical device lumen extends through the device to the medical device distal end.

3. The medical device of claim 2 wherein the medical device comprises an embolic coil.

4. The medical device of claim 1 wherein the medical device comprises a plug.

5. The medical device delivery assembly of claim 1 wherein the delivery portion comprises at least a rigid portion at the delivery portion distal end and a non-rigid portion proximal to the rigid portion.

6. The medical device delivery assembly of claim 5 wherein the at least one notch is formed in the rigid portion.

7. The medical device delivery assembly of claim 5 wherein the non-rigid portion comprises a braid.

8. The medical device delivery assembly of claim 7 wherein the braid comprises at least one of a nickel-titanium alloy, tungsten, and a polymer.

9. The medical device delivery assembly of claim 1 wherein the mandrel comprises a flexible material.

10. The medical device delivery assembly of claim 9 wherein the mandrel distal end of the mandrel is threaded.

11. The medical device delivery assembly of claim 9 wherein the mandrel comprises a nickel-titanium alloy.

12. The medical device of claim 1 wherein the number of at least one prongs is two.

13. The medical device delivery assembly of claim 1, wherein the at least one prong extends longitudinally from the medical device.

14. A kit for deploying a medical device to a body cavity comprising:
   a medical device to be deployed, the medical device extending from a medical device proximal end to a medical device distal end, the medical device proximal end comprising a lumen and a medical device outer surface, at least one prong being attached to the medical device outer surface of the medical device proximal end;
   a sheath for positioning the medical device in the body cavity comprising a delivery portion extending from a sheath proximal end to a sheath distal end, the delivery portion having a sheath lumen and a sheath outer surface, the sheath lumen being sized so as to fit the medical device proximal end therein, the sheath distal end having at least one notch for receiving the at least one prong of the medical device to be deployed such that when the at least one prong is engaged with the at least one notch, the medical device and the delivery portion rotate together bidirectionally; and
   a mandrel extending from a mandrel proximal end to a mandrel distal end, the mandrel being slidably disposed within the sheath lumen, the mandrel distal end fitting within the medical device interior lumen of the first proximal end of the medical device to be deployed, the mandrel distal end being threaded.

15. The kit of claim 14 wherein the mandrel distal end is provided threaded into the medical device lumen at the medical device proximal end.

16. The kit of claim 14, wherein the at least one prong extends longitudinally from the medical device.

* * * * *